United States Patent [19]

Okamura

[11] Patent Number: 5,069,225
[45] Date of Patent: Dec. 3, 1991

[54] BLOOD COLLECTION AND/OR INJECTION DEVICE AND DOUBLE-ENDED MEDICAL NEEDLE AND HOLDER THEREFOR

[75] Inventor: Toshio Okamura, Yamanashi, Japan
[73] Assignee: Terumo Kabushiki Kaisha, Tokyo, Japan
[21] Appl. No.: 412,183
[22] Filed: Sep. 25, 1989

[30] Foreign Application Priority Data

Sep. 28, 1988 [JP] Japan .................. 63-242684
Sep. 29, 1988 [JP] Japan .................. 63-245596

[51] Int. Cl.⁵ .......................................... A61B 5/00
[52] U.S. Cl. ................... 128/765; 604/187; 604/240; 604/243; 604/412; 604/413
[58] Field of Search ........... 604/187, 192, 240, 241, 604/243, 232, 165, 166, 272, 276, 413, 415, 403, 411, 414; 128/763, 765

[56] References Cited

U.S. PATENT DOCUMENTS

| Re. 29,656 | 6/1978 | Chittenden et al. | 604/413 |
| 2,874,694 | 2/1959 | Blackman | 604/232 |
| 4,568,336 | 2/1986 | Cooper | 604/240 |
| 4,799,926 | 1/1989 | Haber | 604/187 |
| 4,840,619 | 6/1989 | Hughes | 604/187 |
| 4,856,533 | 8/1989 | Anrako et al. | 604/403 |

FOREIGN PATENT DOCUMENTS

| 0248979 | 12/1987 | European Pat. Off. | 604/243 |
| 3339705 | 5/1985 | Fed. Rep. of Germany | 604/272 |
| 62-148646 | 7/1987 | Japan . | |
| 1191634 | 5/1970 | United Kingdom | 604/192 |

Primary Examiner—Stephen C. Pellegrino
Assistant Examiner—Robin R. Longo
Attorney, Agent, or Firm—Frishauf, Holtz, Goodman & Woodward

[57] ABSTRACT

A blood collection and/or injection device includes a double-ended medical needle including a cannula having opposite pointed ends, a hub fitted over the cannula, a rubber sheath optionally fitted over an end portion of the cannula, a cylindrical holder having an opening defined in one end thereof, the end portion of the cannula which is optionally covered with the rubber sheath being adapted to be inserted into the opening with the hub held in the opening by the cylindrical holder, and an evacuated blood collection tube or syringe adapted to be inserted into the cylindrical holder through an opening defined in the opposite end of the cylindrical holder and pierced by the end portion of the cannula. The hub has spreading teeth, and the cylindrical holder includes a holder casing having chuck teeth spreadable radially outwardly by the spreading teeth of the hub. The cylindrical holder also includes a ring having recesses for receiving the spreading teeth, and a cap engaging portion is provided on the ring for receiving a cap thereon.

13 Claims, 11 Drawing Sheets

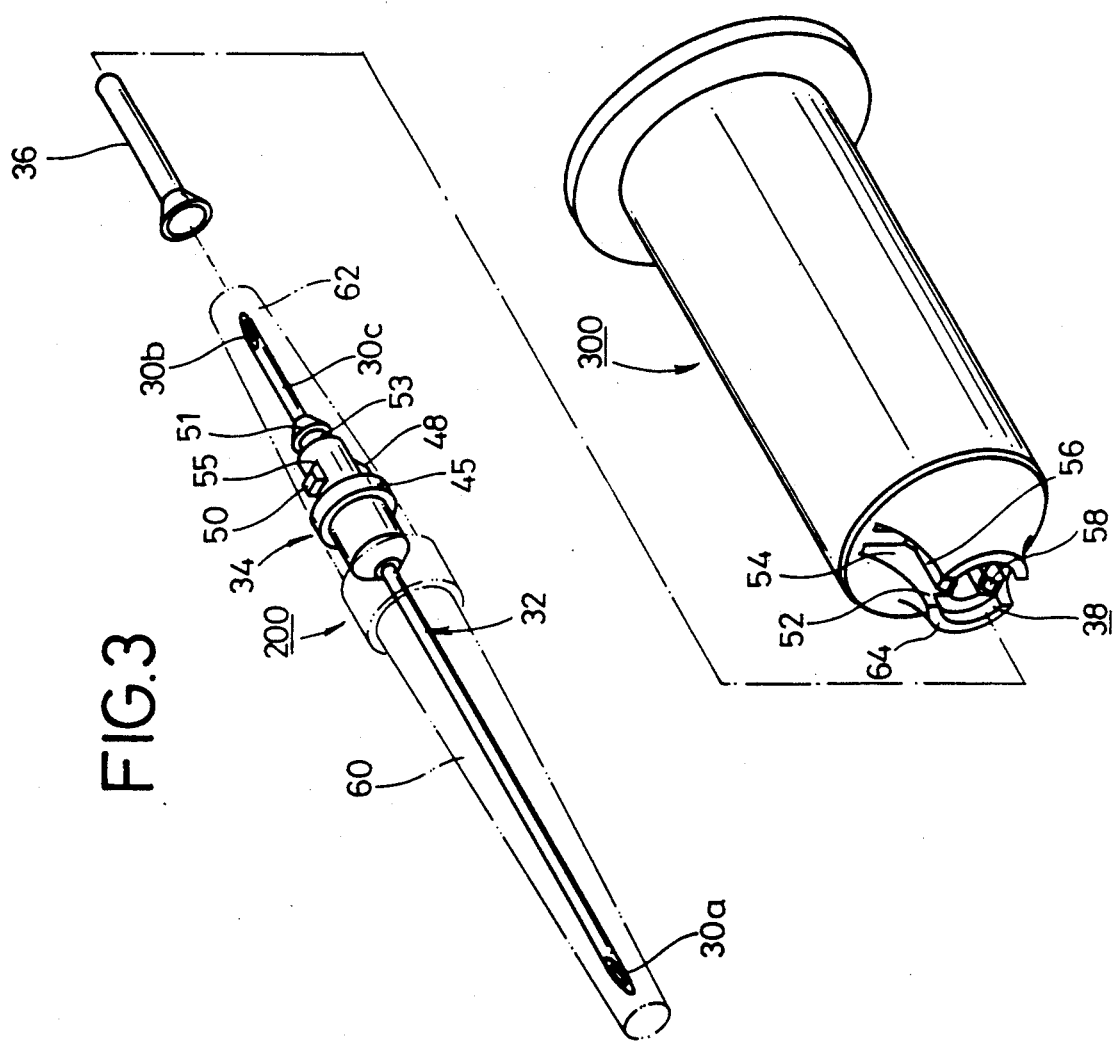

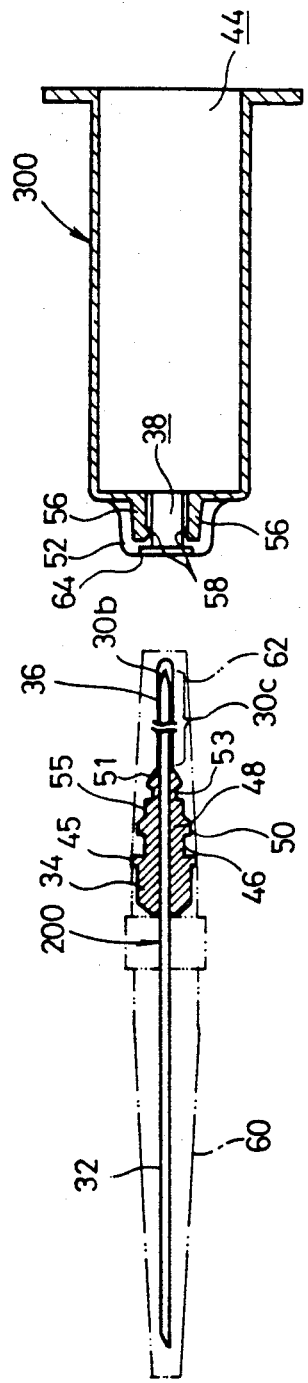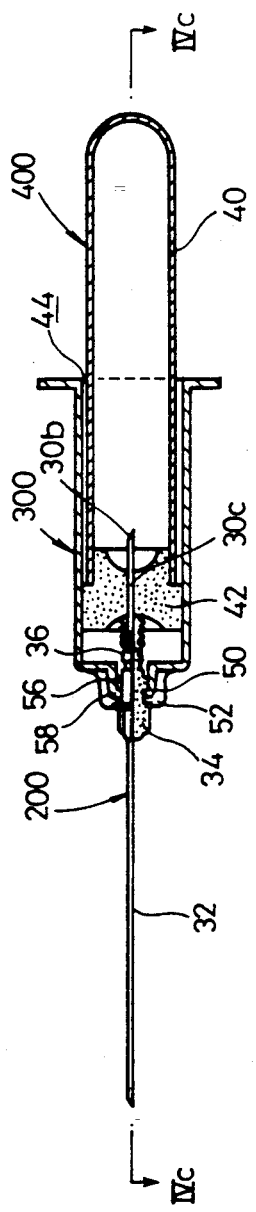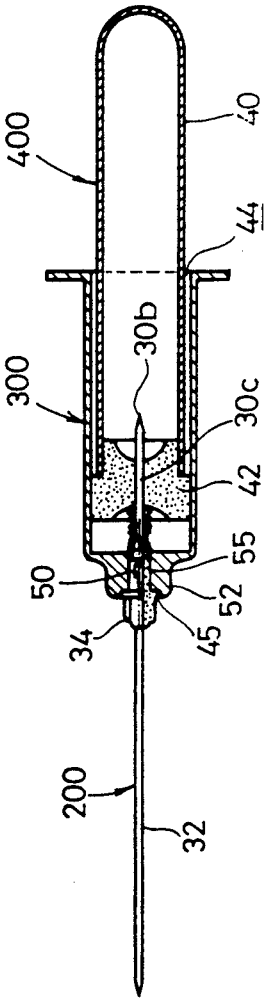

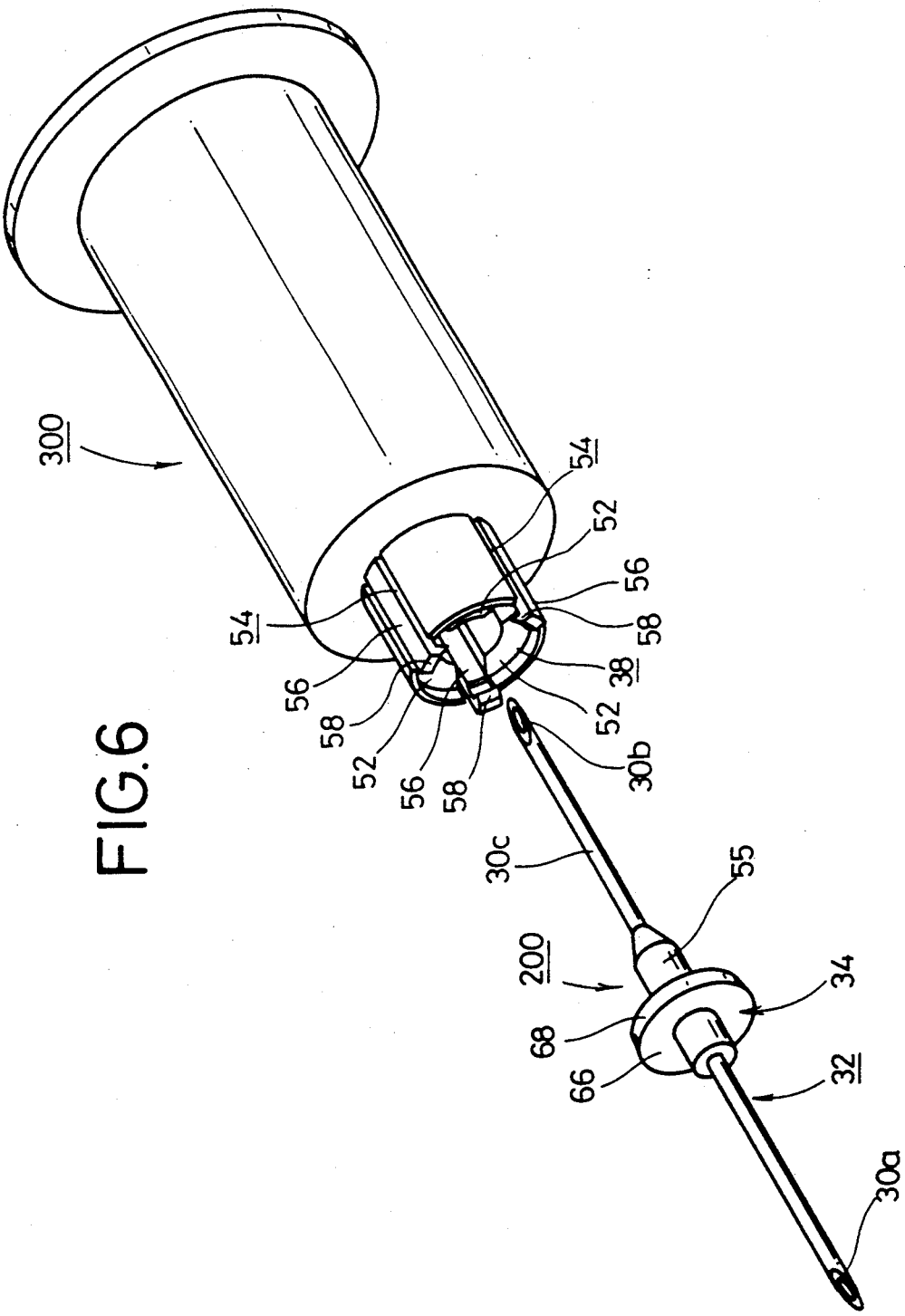

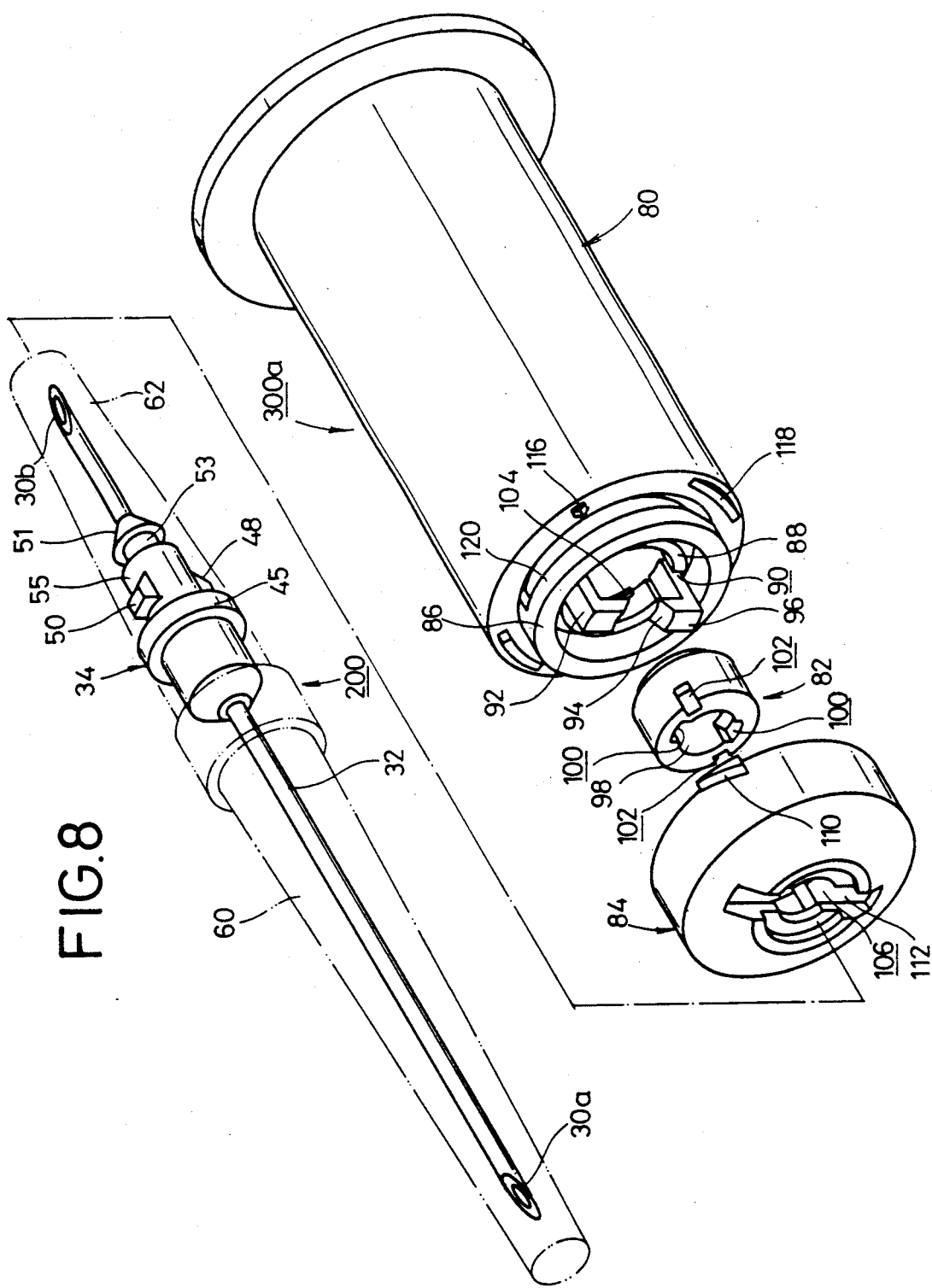

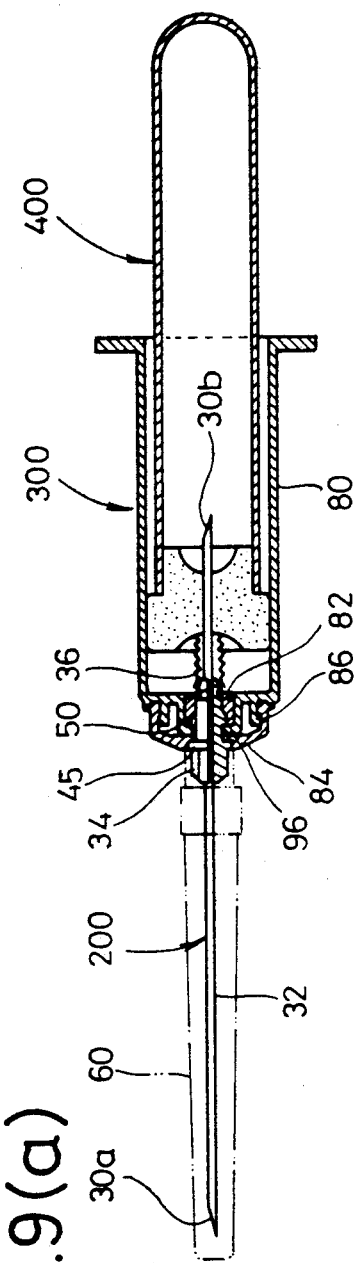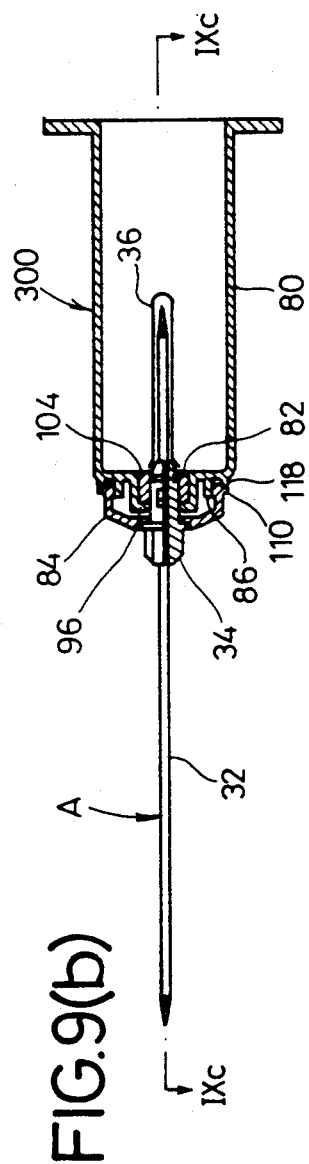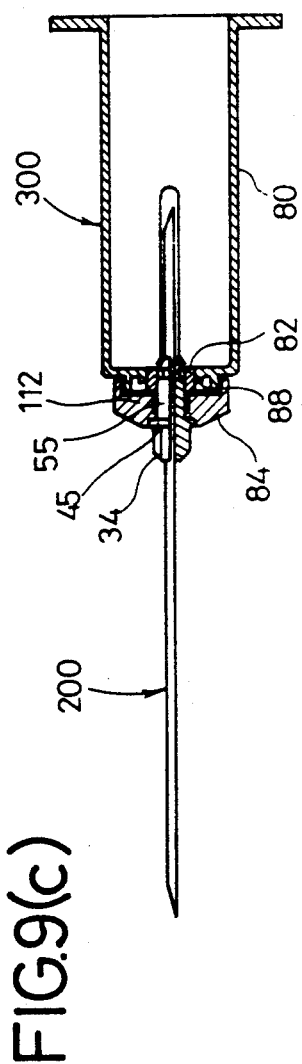

BLOOD COLLECTION AND/OR INJECTION DEVICE AND DOUBLE-ENDED MEDICAL NEEDLE AND HOLDER THEREFOR

BACKGROUND OF THE INVENTION

The present invention relates to a double-ended medical needle and a holder therefor, and a blood collection and/or injection device which employs such a double-ended medical needle and a holder therefor, and more particularly to an improvement in a hub/holder connector structure which comprises a double-ended medical needle including a cannula which has opposite pointed ends, with a hub fitted over the cannula, a tubular holder for holding the hub of the medical needle, and an evacuated blood collection tube or syringe insertable into the holder through an opening thereof for communication with the cannula of the medical needle.

Heretofore, there have widely been employed devices for collecting blood samples from or injecting medicine into human bodies through double-ended medical needles.

FIG. 1 of the accompanying drawings illustrates one such conventional evacuated blood collection device, and FIG. 2 shows a conventional injection/blood collection device.

The evacuated blood collection device shown in FIG. 1 comprises a medical needle 2, a holder 4, and an evacuated blood collection tube 6. The injection/blood collection device shown in FIG. 2 comprises a medical needle 2, a holder 4, and a syringe 8. The medical needles 2 and the holders 4 shown in FIGS. 1 and 2 are of identical structures, respectively.

The medical needle 2 comprises a cannula 10 having opposite pointed ends 10a, 10b, a hub 12 fitted over an intermediate portion of the cannula 10 and supporting the same, and a rubber sheath 14 fitted over an end portion of the cannula 10 and joined to one end of the hub 12. Since the rubber sheath 14 is fitted over the end portion of the cannula 10, the rubber sheath 14 prevents blood from flowing into the holder 4 when blood samples are collected successively into a plurality of evacuated blood collection tube 6 while the cannula 10 is being inserted in a blood vessel.

The holder 4 holds the medical needle 2 through the hub 12, and is in the form of a hollow cylinder made of a transparent plastic material or the like.

The evacuated blood collection tube 6 comprises a bottomed glass tube 16 and a rubber plug 18 closing the open end of the glass tube 16, the rubber plug 18 being penetratable by the cannula 10. Normally, the interior space of the glass tube 16 is evacuated so that it can draw and collect a necessary amount of blood.

The syringe 8 comprises a syringe cylinder 20 and a pusher 24 with a packing 22 mounted on one end thereof. The pusher 24 can be inserted into the syringe cylinder 20 through an open end thereof, with the packing 22 held in close contact with the inner surface of the syringe cylinder 20.

To use the evacuated blood collection device shown in FIG. 1, the medical needle 2 is threaded into the holder 4, and then the evacuated blood collection tube 6 is pushed into the holder 4 through the open end thereof to force one pointed end 10b of the cannula 10 into the rubber plug 18, but not fully through the rubber plug 18. Thereafter, the holder 4 is held by the operator and the other pointed end 10a of the cannula 10 is caused to penetrate a blood vessel in an arm or the like of a blood donor. While the arm and the holder 4 are being fixed relatively to each other, the evacuated blood collection tube 6 is further pushed in to force the pointed end 10b of the cannula 10 all the way through the rubber plug 18, thus allowing blood to flow through the cannula 10 into the evacuated blood collection tube 6.

To use the injection/blood collection device shown in FIG. 2, the medical needle 2 is threaded into the holder 4, and then the syringe 8 is pushed into the holder 4 through the open end thereof until the pointed end 10b of the cannula 10 is inserted into the other open end of the syringe cylinder 20 and positioned therein. The holder 4 is held by the operator and the other pointed end 10a of the cannula 10 is inserted into a blood vessel in an arm or the like of a blood donor or a patient. While the arm and the holder 4 are being fixed relatively to each other, the pusher 24 is pulled out to draw blood through the cannula 10 into the syringe cylinder 10, or the pusher 24 is pushed in to inject medicine from the syringe 8 into the blood vessel. Thereafter, the syringe 8 is pulled out of the holder 4 while the holder 4 is firmly held with respect to the arm, and then a new syringe is connected again to the holder 4.

With the conventional structures described above, however, the palm of a hand or a finger of the operator may be penetrated by the medical needle 2 when it is replaced.

More specifically, in order to remove the medical needle 2 from the holder 4, the medical needle 2 is covered with a protector (not shown), and then the medical needle 2 is unscrewed from the holder 4. When the medical needle 2 is covered with a protector, the palm of a hand or a finger of the operator may be pierced by the medical needle 2. To avoid such an accident, therefore, it is desirable for the operator to be able to throw away only the medical needle 2 without covering the needle 2 with a protector and also without touching the needle 2.

If the needle 2 is not sufficiently threaded into the holder 4, the needle 2 may get loose when the blood collection tube 6 or syringe 8 is connected to the holder 4. It is also troublesome to thread the medical needle 2 into the holder 4. For these reasons, there has been a demand for a structure which facilitates a simple connection between the medical needle 2 and the holder 4.

To meet such a demand, there has been proposed a structure by which a hub and a holder can be connected to each other by an inserting and fitting process as disclosed in Japanese Laid-Open Patent Publication No. 62(1987)-148646. According to the disclosed arrangement, a medical needle can be replaced in one operation so that a blood collection/injection device employing such a medical needle can simply be mounted in place on a blood donor or a patient.

SUMMARY OF THE INVENTION

In view of the aforesaid drawbacks of the conventional blood collection/injection devices, it is an object of the present invention to provide a blood collection and/or injection device which is capable of replacing a medical needle in one operation by connecting a hub and a holder through an inserting and fitting process, and a double-ended medical needle and a holder for use in such a device.

Another object of the present invention is to provide a blood collection and/or injection device which allows a medical needle to be reliably secured in position without the danger of accidental removal simply by strongly inserting a hub of the needle into an end opening in a holder, and a double-ended medical needle and a holder for use in such a device.

Still another object of the present invention is to provide a blood collection and/or injection device which prevents a medical needle and a holder from being separated from each other and permits them to be discarded after use.

Yet another object of the present invention is to provide a blood collection and/or injection device which allows a medical needle to be reliably secured in position without the danger of accidental removal simply by strongly inserting a hub of the needle into an end opening in a holder, but permits the medical needle to be pulled from the holder by twisting a member on the distal end of the holder through a small angle, so that the medical needle can be discarded after use and the holder can be used again, and a double-ended medical needle and a holder for use in such a device.

A further object of the present invention is to provide blood collection and/or injection device comprising a double-ended medical needle, including a cannula having opposite pointed ends, and a hub fitted over said cannula, a cylindrical holder having an opening defined in one end thereof, an end portion of the cannula being adapted to be inserted into said opening with said hub held in said opening by said holder, an evacuated blood collection tube or syringe adapted to be inserted into said holder through an opening defined in the opposite end of said holder and pierced by said end portion of said cannula, said hub having first engaging means, said holder having hub support walls disposed around said opening in said one end of the holder for supporting an end portion of said hub, and second engaging means for engaging said first engaging means, and the arrangement being such that when said end portion of said cannula is inserted into said opening in said one end of the holder, said second engaging means is engaged and spread by said first engaging means, enabling said hub support walls to hold said hub of said medical needle.

A still further object of the present invention is to provide the blood collection and/or injection device wherein said first engaging means comprises spreading teeth projecting radially outwardly from said hub, and said second engaging means comprises flexible walls, the arrangement being such that said spreading teeth can be pushed into said opening in said one end of the holder, said spreading teeth spread said flexible walls radially outwardly and said hub is held under the resiliency of said flexible walls.

A yet further object of the present invention is to provide the blood collection and/or injection device wherein said hub has a smaller-diameter step disposed behind said spreading teeth in the direction in which said spreading teeth are pushed into said opening in said one end of the holder, said flexible walls having chuck teeth on distal ends thereof, the arrangement being such that when said hub is pushed into said holder, said chuck teeth engage said step to prevent said medical needle from being dislodged from said holder.

A further object of the present invention is to provide the blood collection and/or injection device wherein said spreading teeth are angularly spaced from each other by 180° and integrally formed as a pair of spreading teeth with said hub, and said chuck teeth are angularly spaced from each other by 180° and integrally formed as a pair of chuck teeth with a casing of said holder.

Another object of the present invention is to provide a blood collection and/or injection device comprising a double-ended medical needle including a cannula having opposite pointed ends, a hub fitted over said cannula, and a cylindrical holder having an opening defined in one end thereof, an end portion of the cannula being adapted to be inserted into said opening with said hub held in said opening by said holder, an evacuated blood collection tube or syringe adapted to be inserted into said holder through an opening defined in the opposite end of said holder and pierced by said end portion of said cannula, said hub having spreading teeth, and said holder comprising a holder casing having chuck teeth spreadable radially outwardly by said spreading teeth, a ring having recesses for receiving said spreading teeth, and a cap for engaging an engaging portion of said ring.

Still another object of the present invention is to provide the blood collection and/or injection device wherein said hub has a step engageable by said chuck teeth which are spread radially outwardly by said spreading teeth.

Yet another object of the present invention is to provide the blood collection and/or injection device wherein said ring has a hub support hole defined centrally in one end thereof for supporting said hub, said recesses opening into said hub support hole, said engaging portion being defined on an outer surface of said ring, said ring being rotatably and axially immovably positionable radially inwardly of said flexible walls and said spreading teeth.

Yet still another object of the present invention is to provide the blood collection and/or injection device wherein said cap has a noncircular hub insertion hole defined centrally in one end thereof, said cap being adapted to be fitted in said opening in said one end of the holder and angularly movable therein, said cap having a rib disposed therein and engageable with said engaging portion of said ring for angular movement therewith and sliding movement with respect thereto in a direction toward said one end thereof.

A still further object of the present invention is to provide a blood collection and/or injection device comprising a double-ended medical needle including a cannula having opposite pointed ends, a hub fitted over said cannula, a cylindrical holder having an opening defined in one end thereof, an end portion of the cannula being adapted to be inserted into said opening with said hub held in said opening by said holder, an evacuated blood collection tube or syringe adapted to be inserted into said holder through an opening defined in the opposite end of said holder and pierced by said end portion of said cannula, said hub having an engaging flange, said holder having hub support walls disposed around said opening in said one end of the holder for supporting a side wall of said hub, flexible walls separate from said hub support walls, chuck teeth projecting radially inwardly from distal ends of said flexible walls, and a fastening ring axially slidably fitted over said hub support walls and said flexible walls, and the arrangement being such that when said end portion of said cannula is inserted into said opening in said one end of the holder until said engaging flange is held against said hub support walls and thereafter said fastening ring is moved axially, said chuck teeth are flexed radially inwardly to engage said engaging flange of said hub against dislodgment.

A still further object of the present invention is to provide a medical needle comprising a cannula having opposite pointed ends, a hub fitted over said cannula, and an hub having a step near said end portion of said cannula and spreading teeth near said end portion of said cannula.

A yet further object of the present invention is to provide the medical needle wherein said spreading teeth are formed as a pair of spreading teeth which are angularly spaced from each other by at least 180°.

A further object of the present invention is to provide a holder for use in a blood collection and/or injection device including a medical needle having a cannula, a hub fitted over the cannula, said holder comprising an end defining a first opening, a portion of the cannula being adapted to be inserted into said first opening with said hub held in said first opening by said holder, an opposite end defining a second opening for receiving therein an evacuated blood collection tube or syringe, hub support walls disposed around said first opening for supporting an end portion of said hub, said hub support walls having engaging means, and the arrangement being such that when the portion of the cannula which is covered with said rubber sheath is inserted into said first opening, said engaging engaging portions of said hub support walls engages engaging means of said hub to prevent the medical needle from being removed.

Another object of the present invention is to provide the holder wherein said engaging means of said hub support walls comprises engaging teeth or engaging recesses.

Still another object of the present invention is to provide a holder for use with a medical needle having a cannula, a hub fitted over the cannula, said holder comprising an end defining a first opening, a portion of the cannula being adapted to be inserted into said first opening with said hub held by an end of said holder, an opposite end defining a second opening for receiving therein an evacuated blood collection tube or syringe, hub support walls disposed around said first opening for supporting a side wall of said hub, flexible walls disposed around said first opening and separated from said hub support walls by slits, said flexible walls being flexible at least distal ends thereof, and chuck teeth disposed around said first opening and projecting radially inwardly from said flexible walls near the distal ends thereof, said chuck teeth being spreadable radially outwardly by engaging means of said hub to prevent the medical needle from being removed when said engaging means has moved past said chuck teeth.

Yet another object of the present invention is to provide a holder for use with a medical needle having a cannula, a hub fitted over the cannula and having spreading teeth, said holder comprising an end defining a first opening, a portion of the cannula which is covered with being adapted to be inserted into said first opening with said hub held by an end of said holder, an opposite end defining a second opening for receiving therein an evacuated blood collection tube or syringe, a holder casing having flexible walls flexible at distal ends thereof, and chuck teeth projecting radially inwardly from distal ends of said flexible walls and spreadable radially outwardly by the spreading teeth of the hub of the medical needle, a ring having a central hub support hole and disposed rotatably and axially immovably inside of said flexible walls and said chuck teeth of said holder casing, and a cap having a central hub insertion hole and fitted angularly movably over said holder casing, said cap having a rib engageable with said ring for angular movement therewith and sliding movement with respect thereto in a direction toward a distal end thereof.

Yet still another object of the present invention is to provide a holder for use with a medical needle having a cannula, a hub fitted over the cannula and having spreading teeth, said holder comprising an end defining a first opening, a portion of the cannula which is covered with being adapted to be inserted into said first opening with said hub held in said first opening by said holder, an opposite end defining a second opening for receiving therein an evacuated blood collection tube or syringe, hub support walls disposed around said first opening for supporting a side wall of said hub, flexible walls disposed around said first opening and separated from said hub support walls by slits, said flexible walls being flexible at distal ends thereof, chuck teeth disposed around said first opening and projecting radially inwardly from distal ends of said flexible walls, a fastening ring axially slidably fitted over said hub support walls and said flexible walls, and the arrangement being such that when said portion of said cannula is inserted into said first opening until an engaging flange of said hub is held against said hub support walls and thereafter said fastening ring is moved axially, said chuck teeth are flexed radially inwardly to engage said engaging flange of said hub against dislodgment.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 3 is an exploded perspective view of a blood collection and/or injection device which employs a double-ended medical needle and a holder therefor according to a first embodiment of the present invention;

FIG. 4(a) is a longitudinal cross-sectional view showing the condition in which the double-ended medical needle shown in FIG. 3 is about to be inserted into the holder;

FIG. 4(b) is a longitudinal cross-sectional view showing the condition in which the double-ended medical needle is inserted in the holder and an evacuated blood collection tube is attached;

FIG. 4(c) is a longitudinal cross-sectional view taken along line IVc—IVc of FIG. 4(b);

FIG. 6 is an exploded perspective view of a blood collection and/or injection device which employs a double-ended medical needle and a holder therefor according to a second embodiment of the present invention;

FIG. 8 is an exploded perspective view of a blood collection and/or injection device which employs a double-ended medical needle and a holder therefor according to third embodiment of the present invention;

FIG. 9(a) is a longitudinal cross-sectional view showing the condition in which the double-ended medical needle shown in FIG. 8 is inserted in the holder and an evacuated blood collection tube is attached;

FIG. 9(b) is a longitudinal cross-sectional view showing the condition in which the medical needle can be pulled from the holder;

FIG. 9(c) is a longitudinal cross-sectional view taken along line IXc—IXc of FIG. 9(b);

DETAILED DESCRIPTION OF THE PREFERRED EMBODIMENTS

Figure 1:
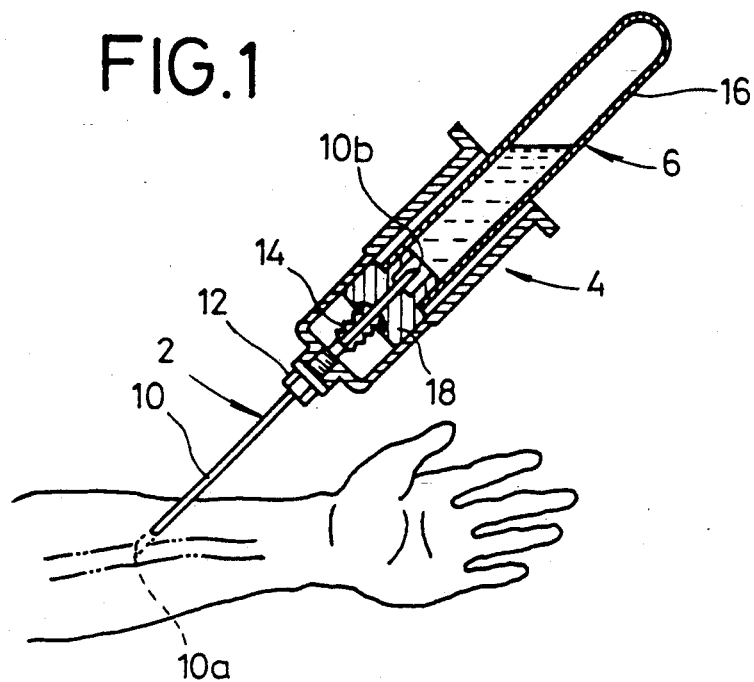
FIG. 1 is a longitudinal cross-sectional view of a conventional evacuated blood collection device.
Figure 2:
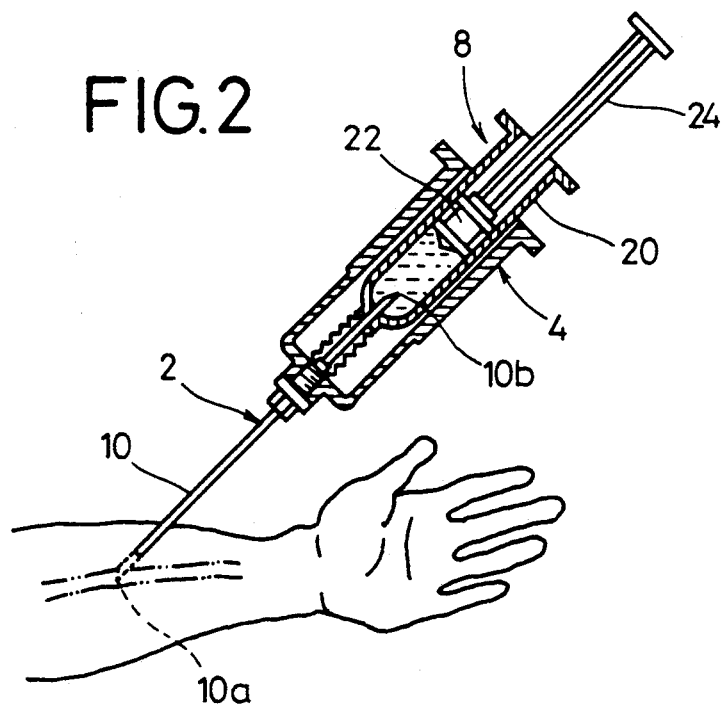
FIG. 2 is a longitudinal cross-sectional view of another conventional evacuated blood collection device.
Figure 5A:
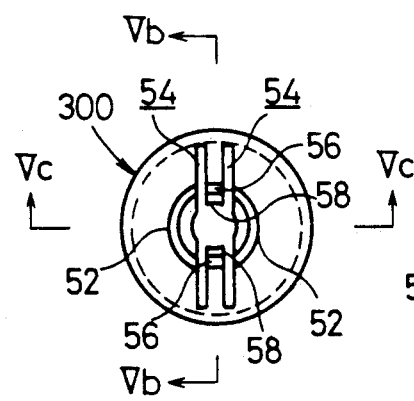
FIG. 5(a) is a front elevational view of the holder.
Figure 5B:
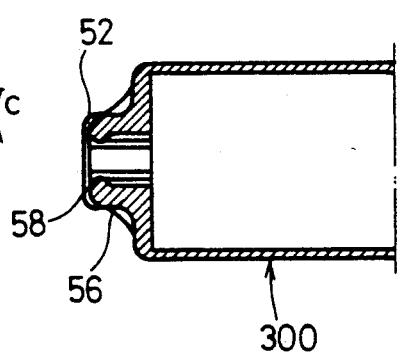
FIG. 5(b) is a fragmentary cross-sectional view taken along line Vb—Vb of FIG. 5(a)
Figure 5C:
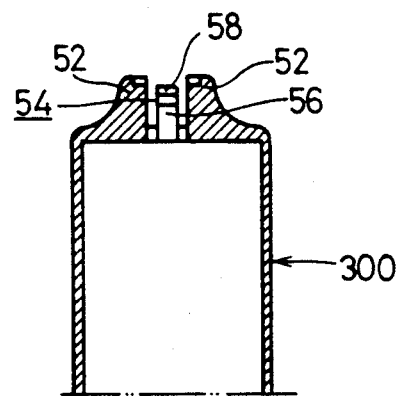
FIG. 5(c) is a fragmentary cross-sectional view taken along line Vc—Vc of FIG. 5(a)

Like or corresponding reference numerals denote like or corresponding parts throughout views.

FIGS. 3, 4(a) through 4(c), and 5(a) through 5(c) show a blood collection and/or injection device employing a double-ended medical needle and a holder therefor according to a first embodiment of the present invention. The blood collection and/or injection device comprises a double-ended medical needle 200, a holder 300, and an evacuated blood collection tube 400. The blood collection and/or injection device may employ a syringe (not shown) in place of the evacuated blood collection tube 400.

The double-ended medical needle 200 has a cannula 32 of stainless steel which has opposite pointed ends 30a, 30b. A hub 34 is fitted over an intermediate portion of the cannula 32. A sheath 36 of rubber is fitted over an end portion 30c of the cannula 32 and has an end fitted over an end of the hub 34.

The holder 300 is in the form of a hollow cylinder having an opening 38 defined in one end thereof. The end portion 30c of the cannula 32 over which the rubber sheath 36 is fitted is inserted through the opening 38, with the hub 34 being held by the end of the holder 300. The holder 300 will be gripped by the operator when in use.

The evacuated blood collection tube 400 comprises a bottomed tube 40 of glass and a plug 42 of rubber closing the open end of the glass tube 40 and penetratable by the cannula 32. The interior space of the tube 40 is evacuated so that it can collect a necessary amount of blood under a vacuum. The rubber plug 42 is inserted into the holder 300 through an opening 44 defined in the other end thereof until the plug 42 is pierced by the end portion 30c of the cannula 32.

The hub 34 of the medical needle 200 has a flange 45 formed as a radially outward step in a position closer to the end portion 30c. The hub 34 also has a pair of diametrically opposite spreading teeth 50 on a position closer to the end portion 30c than the flange 45. Each of the spreading teeth 50 has a step 46 facing the pointed end 30a and a slanted surface 48 facing the end portion 30c and serving as a wedge. The hub 34 also includes a tapered head 51 on its distal end near the end portion 30c and a cylindrical side wall 55 positioned near the spreading teeth 50, with an annular step or groove 53 being defined between the tapered head 51 and the cylindrical wall 55. The side wall 55 is joined to the slanted surfaces 48.

Around the opening 38 of the holder 300, there are provided two hub support walls 52 for engaging the spreading teeth 50 of the hub 34, two flexible walls 56 separated from the hub support walls 52 by slits 54 and having slightly flexible distal ends, the flexible walls 56 having wall surfaces displaced radially inwardly of the hub support walls 52, and two chuck teeth 58 projecting as engaging teeth radially inwardly from the distal ends of the flexible walls 56.

The medical needle 200 is stored in a protective case 60 and a protective cap 62 when it is offered for sale. In use, the protective cap 62 is removed to expose the cannula end portion 30c of the needle 200, and the protective case 60 is left on the needle 200. While holding the protective case 60, the needle 200 is pushed into the holder 300 so that the end portion 30c of the cannula 32 which is covered with the rubber sheath 36 passes through the opening 38 of the holder 300. As a result, the spreading teeth 50 of the hub 34 slide against and spread radially outwardly the chuck teeth 58 on the distal end of the flexible wall 56 in the opening 38 of the holder 300. When the spreading teeth 50 have moved past the chuck teeth 58, the steps 46 positioned behind the spreading teeth 50 intimately engage the chuck teeth 58, and the flange 45 of the hub 34 abuts against an end surface 64 of the hub support walls 52 which defines the opening 38 of the holder 300. Thus, the needle 200 is made axially immovable and hence cannot be removed from the holder 300. Then, the protective case 60 is detached from the needle 200, making the needle 200 ready for use.

Figure 7A:
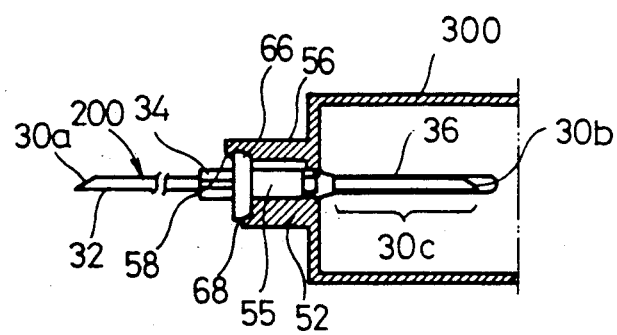
FIG. 7(a) is a fragmentary longitudinal cross-sectional view showing the condition in which the double-ended medical needle shown in FIG. 6 is attached to the holder.
Figure 7B:
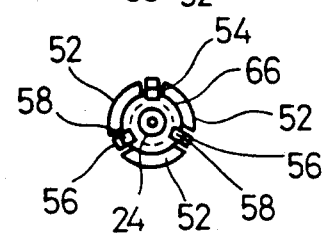
FIG. 7(b) is a cross-sectional view taken along line VIIb—VIIb of FIG. 7(a)

FIGS. 6, 7(a) and 7(b) show a blood collection and/or injection device employing a double-ended medical needle and a holder therefor according to a second embodiment of the present invention. The blood collection and/or injection device of the second embodiment comprises a double-ended medical needle 200, a holder 300, and either an evacuated blood collection tube (which is identical to the tube 400 shown in FIGS. 4(a) and 4(b)) or a syringe.

The double-ended medical needle 200 has a cannula 32 which has opposite pointed ends 30a, 30b, with hub 34 is fitted over an intermediate portion of the cannula 32. A sheath 36 of rubber is fitted over a distal end portion 30c of the cannula 32. The hub 34 has an engaging flange 66 positioned closer to the other end of the cannula 32. The flange 66 has a tapered circumferential surface 68 progressively reduced in diameter in one axial direction.

The holder 300 has an opening 38 in one end thereof through which the cannula end portion 30c covered with the rubber sheath 36 passes. The holder 300 holds the hub 34 at the end thereof, and also holds the evacuated blood collection tube or the syringe which is inserted through an opening in the other end of the holder 300. Around the opening 38 of the holder 300, there are disposed three hub support walls 52 each having an arcuate axial cross-sectional shape, three flexible walls 56 disposed between the hub support walls 52, and three chuck teeth 58 projecting radially inwardly from the distal ends of the flexible walls 56. The hub support walls 52 support a side wall 55 of the hub 34 which is fitted therein, and also support the flange 66 in engagement therewith. The flexible walls 56 comprise wall sections separated from the hub support walls 52 by slits 54, and are slightly flexible at their distal ends.

The three chuck teeth 58 are circumferentially spaced from each other by 120°. Each of the chuck teeth 58 has a triangular shape projecting radially inwardly from the distal end of one of the flexible walls 56. The chuck teeth 58 are spread apart by the engaging flange 66 of the hub 34 when the needle 200 is inserted into the holder 300. When the engaging flange 66 have moved past the chuck teeth 58, the engaging flange 66 and the chuck teeth 58 are inseparably held in locking engagement with each other.

In use, a protective case 60 on the needle 200 is held, and the needle 200 is pushed into the holder 300 so that the end portion 30c of the cannula 32 which is covered with the rubber sheath 36 passes through the opening 38 of the holder 300. The engaging flange 66 of the hub 34 slides against and spreads radially outwardly the chuck teeth 58 of the holder 300. Upon the flange 66 moving over the chuck teeth 58, the flange 66 is closely engaged by the chuck teeth 58. Therefore, the needle 200 can no longer be pulled out of the holder 300. At this time, the flange 66 is held against the distal ends of the hub support walls 52.

FIGS. 8 through 13(a) and 13(b) show a blood collection and/or injection device employing a double-ended medical needle and a holder therefor according to a third embodiment of the present invention. The blood collection and/or injection device comprises a double-ended medical needle 200, a holder 300, and an evacuated blood collection tube 400. The blood collection and/or injection device may employ a syringe (not shown) in place of the evacuated blood collection tube 400.

Figure 10A:
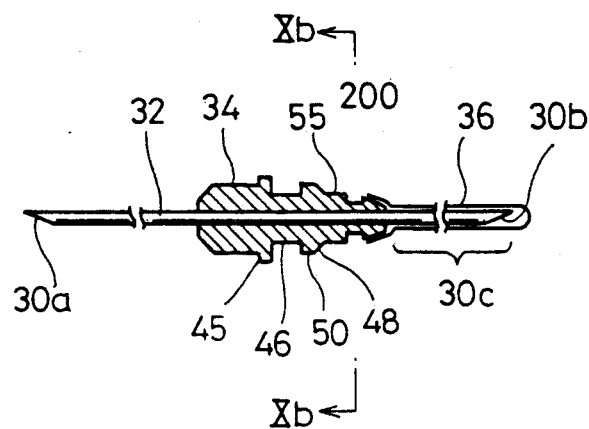
FIG. 10(a) is a longitudinal cross-sectional view of a double-ended medical needle according to the third embodiment of the present invention.
Figure 10B:
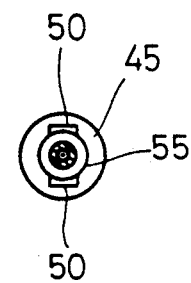
FIG. 10(b) is a cross-sectional view taken along line Xb—Xb of FIG. 10(a)
Figure 11A:
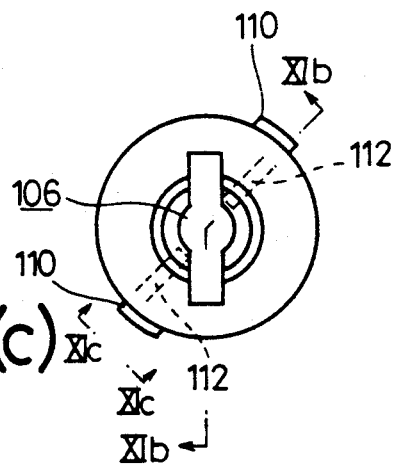
FIG. 11(a) is a front elevational view of a cap according to the third embodiment of the present invention.
Figure 11B:
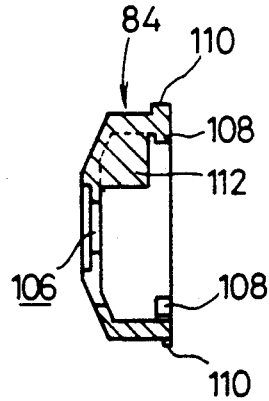
FIG. 11(b) is a cross-sectional view taken along line XIb—XIb of FIG. 11(a)
Figure 11C:
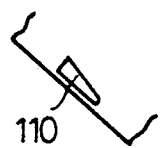
FIG. 11(c) is a view taken alone line XIc—XIc of FIG. 11(a)
Figure 12A:
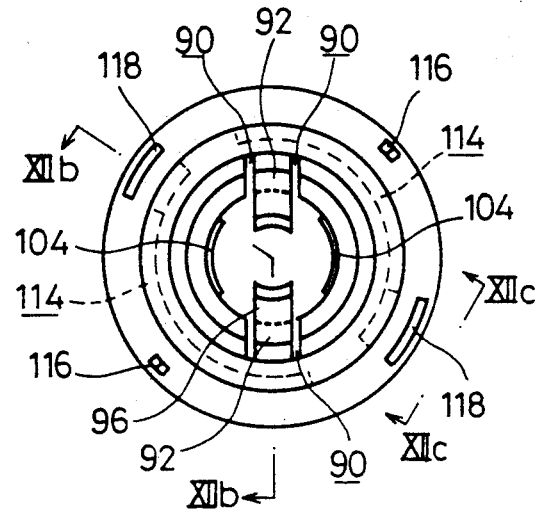
FIG. 12(a) is a front elevational view of a holder casing according to the third embodiment of the present invention.
Figure 12B:
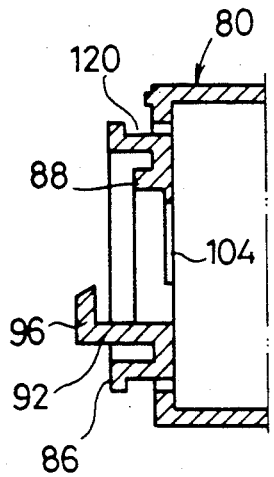
FIG. 12(b) is a cross-sectional view taken along line XIIb—XIIb of FIG. 12(a)
Figure 12C:
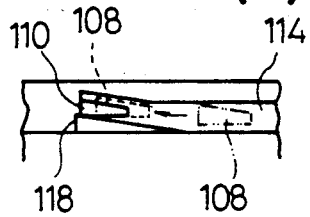
FIG. 12(c) is a view taken along line XIIc—XIIc of FIG. 12(a)

As shown in FIGS. 8, 10(a) and 10(b), the needle 200 has a hub 34 including a flange 45 formed as a radially outward step in a position closer to the end portion 30c of the needle 200. The hub 34 also has a pair of diametrically opposite spreading teeth 50 on a position closer to the end portion 30c than the flange 45. Each of the spreading teeth 50 has a step 46 facing the pointed end 30a and a slanted surface 48 facing the end portion 30c and serving as a wedge. Therefore, the medical needle 200 is substantially identical in construction to the medical needle according to the first embodiment.

In order to allow the needle 200 to be pulled out of the holder 300 in one operation, the holder 300 has an end of a much different structure from that of the holder 300 according to the first embodiment.

Figure 13A:
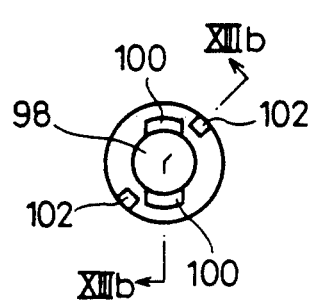
FIG. 13(a) is a front elevational view of a ring according to the third embodiment of the present invention.
Figure 13B:
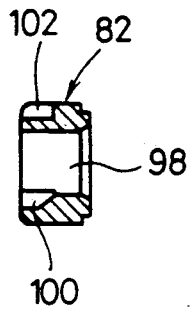
FIG. 13(b) is a cross-sectional view taken along line XIIIb—XIIIb of FIG. 13(a)

The holder 300a basically comprises a holder casing 80 shown in FIGS. 8, 9(c) through 9(c), 12(a) and 12(b), a ring 82 shown in FIGS. 8, 13(a) and 13(b), and a cap 84 shown in FIGS. 8, 11(a) through 11(c).

As shown in FIGS. 8, 12(a) through 12(c), the holder casing 80 has an outer cylindrical wall 86 of a reduced diameter on the end thereof, and an inner cylindrical wall 88 disposed radially inwardly of the outer cylindrical wall 86, the inner cylindrical wall 88 being axially shorter than the outer cylindrical wall 86. The inner cylindrical wall 88 is circumferentially divided into independent walls by slits 90 and has two internal flexible walls 92 extending axially from the independent walls and slightly flexible at their distal ends. The two flexible walls 92 are diametrically opposite to each other and circumferentially spaced from each other by 180°. The flexible walls 92 have respective chuck teeth 96 projecting radially inwardly from the distal ends thereof and having slanted surfaces 94 which enable the chuck teeth 96 to act as wedges. The chuck teeth 96 are spreadable radially outwardly.

As shown in FIGS. 8, 13(a) and 13(b), the ring 82 has a hub support hole 98 defined centrally therein and extending axially, and a pair of diametrically opposite engaging recesses 100 opening radially inwardly and serving to receive the spreading teeth 50 of the hub 34. The engaging recesses 100 are open into the hub support hole 98 and are 180° spaced from each other. The ring 82 also has a pair of 180° spaced engaging recesses 102 defined in the outer circumferential surface thereof. The engaging recesses 102 are angularly spaced from the respective engaging recesses 100 by about 45° in the clockwise direction (FIG. 13(a)). When the ring 82 is inserted into the opening of the holder casing 80 and rotatably placed in the inner cylindrical wall 88 of the holder casing 80, the ring 82 is held against axial movement by the chuck teeth 96 and a pair of arcuate engaging ridges 104 projecting radially inwardly from the inner ends of the inner cylindrical wall 88.

As shown in FIGS. 8, 11(a) through 11(c), the cap 84 has a noncircular hub insertion hole 106 defined centrally therein, a pair of radially inward projections 108 on the inner surface of an opening defined in the cap 84 remote from the hub insertion hole 106, and a pair of flanges 110 projecting radially outwardly from the outer circumferential surface in radial alignment with the projections 108, respectively. A plurality of, preferably two, ribs 112 are disposed on the inner surface of the cap 84.

To place the cap 84 on the holder casing 80, the cap 84 is forcibly pushed axially into covering relation to the outer cylindrical wall 86 of the holder casing 80 while the chuck teeth 96 are being held in alignment with the hub insertion hole 106. The projections 108 of the cap 84 are fitted respectively into two grooves defined in the outer surface of the outer cylindrical wall 86 of the holder casing 80, and the flanges 110 engage two triangular stoppers 116, respectively, on the distal end surface of a larger-diameter portion of the holder casing 80. The cap 84 is therefore prevented from rotating by the stoppers 116. The ribs 112 are fitted in the recesses 102 of the ring 82, so that the cap 84 and the ring 82 are combined together. When the cap 84 is rotated clockwise, the flanges 110 are held against the stoppers 116, respectively. Upon rotation of the cap 84 through about 90°, the flanges 110 ride over arcuate ridges 118, respectively, on the distal end surface of the larger-diameter portion of the holder casing 80. Each of the arcuate ridges 118 is tapered such that its thickness is progressively increased in the clockwise direction. The projections 108 enter progressively wider end portions of a groove 120 defined in the outer surface of the outer cylindrical wall 86, whereupon the cap 84 is locked on the holder casing 80. At the same time, the ribs 112 transmit the clockwise rotation of the cap 84 to the ring 82, and are slid slightly axially toward the distal end of the holder 300 in a direction out of the recesses 102. However, the ring 82 and the cap 84 are not separated from each other.

Therefore, when the cap 84 is forcibly pushed toward and attached to the holder casing 80, the cap 84 is prevented from wobbling axially and rotating about its own axis. As a result, the hub 34 of the needle 200 can easily and sufficiently be fitted in the holder 300. With the needle 200 installed, when the cap 84 is rotated about 90° in the clockwise direction, as described above, the cap 84 is slightly moved axially toward the distal end of the holder 300, and the ring 82 rotates in unison with the cap 84, causing the hub 34 supported by the ring 32 to rotate the needle 200. The spreading teeth 50 of the hub 34 are also rotated clockwise out of engagement with the chuck teeth 96 of the holder casing 80. At this time, because the spreading teeth 50 of the hub 34 and the hub insertion hole 106 of the cap 84 are not rotated relatively to each other, the spreading teeth 50 can be withdrawn through the hub insertion hole 106, and hence the needle 20 can be pulled out of the holder 300. In the illustrated embodiment, the ribs 112 of the cap 84 enter the recesses 102, respectively, of the ring 82. However, ribs may be formed on the ring 82 and recesses for receiving the ribs may be formed in the cap 84.

The medical needle 200 is stored in a protective case 60 and a protective cap 62 when it is offered for sale. In use, the protective cap 62 is removed to expose the cannula end portion 30c of the needle 200, and the protective case 60 is left on the needle 200. While holding the protective case 60, the needle 200 is pushed into the holder 300 so that the end portion 30c of the cannula 32 which is covered with the rubber sheath 36 passes through the opening of the holder 300. As a result, the spreading teeth 50 of the hub 34 spread radially outwardly the chuck teeth 96 of the holder casing 80 and enter the respective recesses 100 of the ring 82, and the end portion of the hub 34 is fitted in the hub support hole 98 of the ring 82. When the spreading teeth 50 have moved past the chuck teeth 96, the spreading teeth 50 and the chuck teeth 96 are securely locked by each other, and the flange 44 of the hub 34 is held against the cap 84. The medical needle 200 is made axially immovable and hence cannot be removed from the holder 300.

After the device has been used, the cap 84 is rotated with respect to the holder casing 80 through a certain angle in a direction to become loose, i.e., counterclockwise, whereupon the needle 200 is rotated through the ring 82. The spreading teeth 50 which have prevented the needle 200 from being removed are now angularly displaced out of alignment with the respective chuck teeth 96. As a consequence, the needle 200 can be pulled from the holder 300.

The structure by which the cap 84 is angularly movably mounted on the holder casing 80 may be of any of various other configurations than illustrated. For example, either one of the outer surface of the outer cylindrical wall 86 and the inner surface of the cap 84 may have a helical groove extending along a quarter or half of a circle, the other may have a ridge for engaging in the helical groove. Alternatively, the outer cylindrical wall 86 may be dispensed with, and the outer surface of the larger-diameter portion of the holder casing 80 may have a helical groove extending along a quarter of a circle whereas the inner surface of the cap 84 which may be sized to fit over the larger-diameter portion of the holder casing 80 may have a ridge for engaging in the helical groove. The helical groove and the ridge may then be interfitted to install the cap 84 angularly movably on the holder casing 80.

Figure 15A:
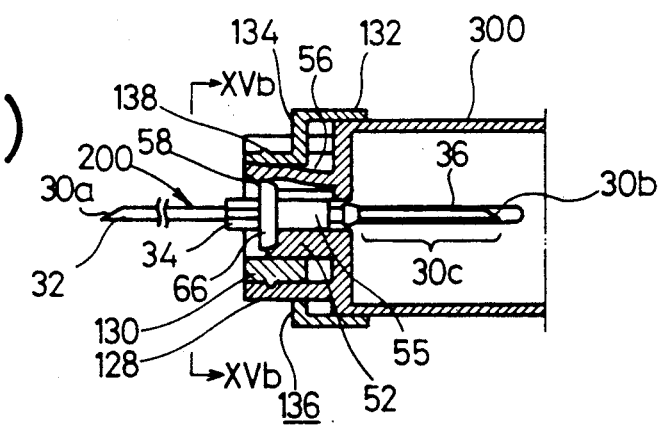
FIG. 15(a) is a fragmentary longitudinal cross-sectional view showing the condition in which the double-ended medical needle shown in FIG. 14 is attached to the holder.
Figure 15B:
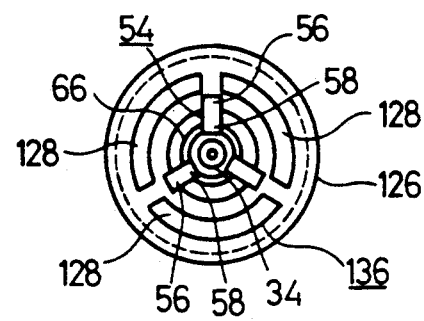
FIG. 15(b) is a cross-sectional view taken along line XVb—XVb of FIG. 15(a).
Figure 14:
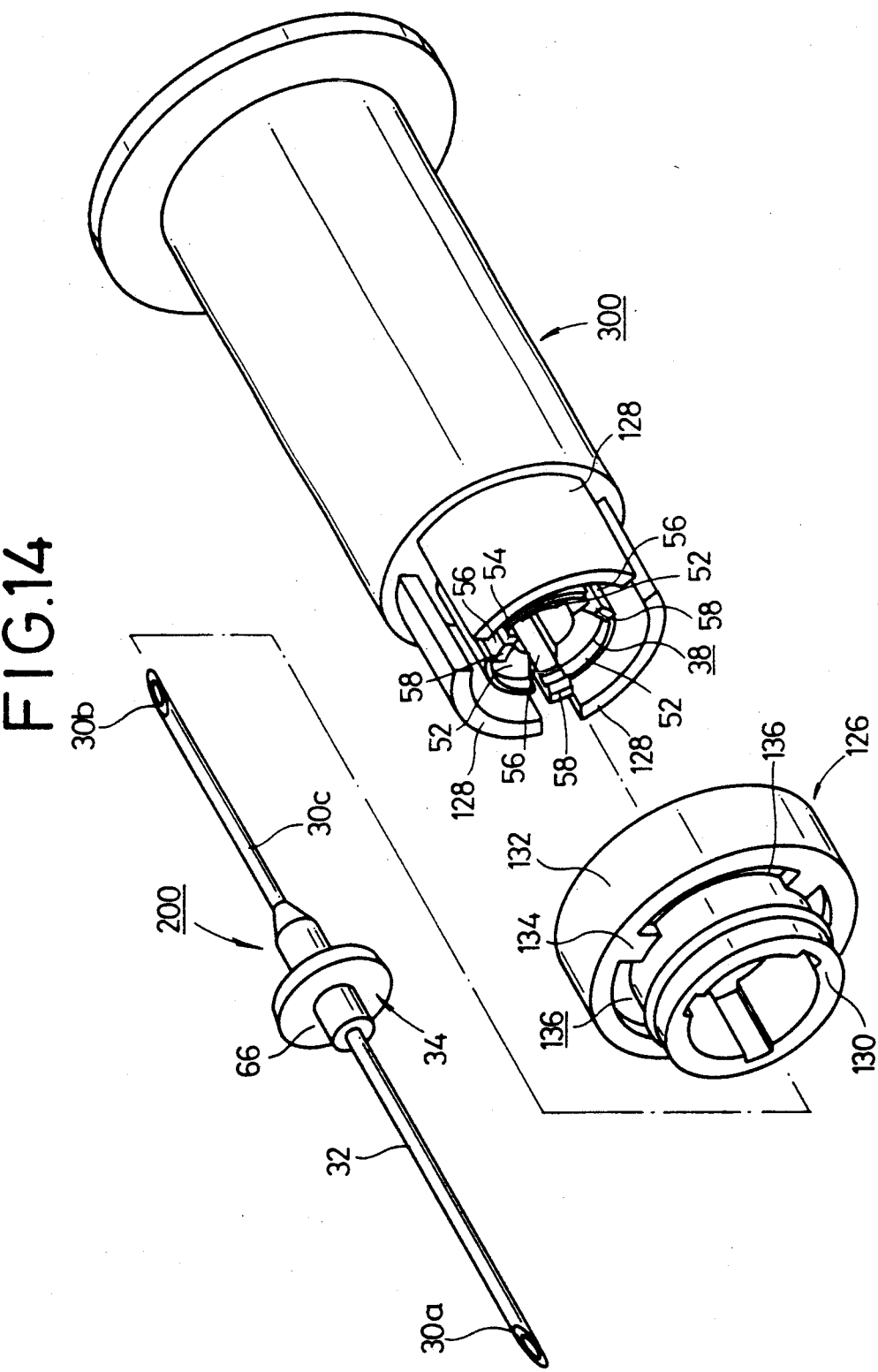
FIG. 14 is an exploded perspective view of a blood collection and/or injection device which employs a double-ended medical needle and a holder therefor according to a fourth embodiment of the present invention.

FIGS. 14, 15(a) and 15(c) show a blood collection and/or injection device employing a double-ended medical needle and a holder therefor according to a fourth embodiment of the present invention. The blood collection and/or injection device comprises a double-ended medical needle 200, a holder 300, and either an evacuated blood collection tube or a syringe.

The double-ended medical needle 200 has a cannula 32 having opposite pointed ends 30a, 30b. A hub 34 is fitted over an intermediate portion of the cannula 32. A sheath 36 of rubber is fitted over an end portion 30c of the cannula 32. The hub 34 has an engaging flange 66 remote from the end portion 30c. Therefore, the medical needle 200 of the fourth embodiment is substantially identical in structure to the medical needle 200 of the first embodiment.

The holder 300 is in the form of a hollow cylinder having an opening 38 defined in one end thereof. The end portion 30c of the cannula 32 over which the rubber sheath 36 is fitted is inserted through the opening 38, with the hub 34 being held by the end of the holder 300. The holder 300 also holds the evacuated blood collection tube or syringe.

Around the opening 38 of the holder 300, there are provided three hub support walls 52 each having an arcuate vertical cross-sectional shape, three flexible walls 56 disposed between the hub support walls 52, and three chuck teeth 58 projecting radially inwardly from the distal ends of the flexible walls 56, and three arcuate guide walls 128 disposed around the hub support walls 52. A fastening ring 126 is fitted over the end of the holder 300.

The hub support walls 52 serve to support the side wall 55 of the hub 34 which extends from the flange 66 toward the end portion 30c.

The flexible walls 56 are separated from the hub support walls 52 by slits 54, and are slightly flexible at their distal ends. The flexible walls 56 have wall surfaces displaced radially inwardly from the hub support walls 52. The chuck teeth 58 project radially inwardly from the distal ends of the flexible walls 56, respectively.

The fastening ring 126 comprises a stepped hollow cylinder including a smaller-diameter cylindrical portion 130 and a larger-diameter cylindrical portion 132. The hub support walls 52 and the flexible walls 56 are housed in the smaller-diameter cylindrical portion 130 of the fastening ring 126. The fastening ring 126 has a stepped wall 134 extending radially between the smaller- and larger-diameter cylindrical portions 130, 132, the stepped wall 134 has three guide openings 136 defined therein and guiding the guide walls 128, respectively, therein. The larger-diameter cylindrical portion 132 is slidably fitted over the distal end of the larger-diameter portion of the holder 300.

To use the device, the end portion 30c of the needle 200 over which the rubber sheath 36 is fitted is inserted into the opening 38 of the holder 300 until the flange 66 abuts against the hub support walls 52, after which the fastening ring 126 is moved so that it will be deeply fitted over the holder 300. As a result, the smaller-diameter cylindrical portion 130 is positioned near the proximal ends of the guide walls 128. At this time, the chuck teeth 58 flex radially inwardly to engage the flange 66 of the hub 34 against dislodgment. A positioning ridge 138 is disposed on the outer circumferential surface of the smaller-diameter cylindrical portion 130. The positioning ridge 138 is seated in recesses defined in the inner surfaces of the guide walls 128, thus keeping the guide walls 128 and the smaller-diameter cylindrical portion 130 in secure engagement with each other.

With the smaller-diameter cylindrical portion 130 positioned near the proximal ends of the guide walls 128 thereby to open the chuck teeth 58, the protective cap is removed from the medical needle 200, exposing the cannula end portion 32c of the needle 200, and the cannula end portion 32c covered with the rubber sheath is inserted into the opening 38 of the holder 300. The flange 66 engages the hub support walls 52, and then the smaller-diameter cylindrical portion 130 of the fastening ring 126 is axially moved toward the distal ends of the guide walls 128, so that the smaller-diameter cylindrical portion 130 and the guide walls 128 are held in firm locking engagement with each other by the positioning ridge 138. Consequently, the flange 66 of the hub 34 is firmly engaged by the chuck teeth 58 against accidental removal.

After the device has been used, the smaller-diameter cylindrical portion 130 is moved toward the proximal ends of the guide walls 128 to open the chuck teeth 58 out of engagement with the flange 66. Then, the medical needle 200 can be pulled from the holder 300 for replacement. The guide walls 128 may be dispensed with.

According to one embodiment of the present invention, as described above, the protective cap is detached to expose the cannula end portion of the needle which is covered with the rubber sheath, and then the protective case is held and the cannula end portion of the needle is forcibly pushed into the opening of the holder. As a consequence, the chuck teeth chuck the step of the hub and are seated on the step, with the hub support walls being fitted over the side wall of the hub.

Therefore, the medical needle can reliably be fixedly mounted in the opening of the holder in one operation. The medical needle is thus prevented from being dislodged when the evacuated blood collection tube is inserted into the holder until the rubber plug of the evacuated blood collection tube is pierced by the pointed end of the needle. The medical needle thus installed is prevented from wobbling axially and laterally. Since the medical needle cannot be pulled out of the holder, it is possible to place the protective case over the distal end portion of the cannula and throw away the entire device after use. The palm of a hand or a finger of the operator is protected from being pierced because the medical needle is not required to be held, loosened, and separated from the holder.

According to a further embodiment of the present invention, when the cannula end portion of the needle which is covered with the rubber sheath is forced into the opening of the holder, the spreading teeth of the hub spread the chuck teeth of the holder casing radially outwardly and enter the respective recesses of the ring, and the end portion of the hub is fitted in the hub support hole of the ring. At the time the spreading teeth have moved past the chuck teeth, the stepped surfaces of the spreading teeth and the chuck teeth are held in intimate locking engagement with each other, thus preventing the needle from being pulled out. The flange of the hub is seated on the distal end surface of the cap. The medical needle can therefore be securely mounted in the opening of the holder in one operation. When the evacuated blood collection tube is inserted into the holder until the rubber plug of the evacuated blood collection tube is pierced by the pointed end of the cannula, the needle is prevented from being dislodged, and from moving axially and laterally.

After the device has been used, the cap is rotated a certain angle in the direction in which it is loosened, causing the ring to rotate the needle. The spreading teeth which have been locked against removal by the chuck teeth are then angularly moved out of axial alignment with the chuck teeth, whereupon the needle can be pulled out of the holder. The needle which has been used is then pulled out of the holder, and is stored back into the protective case and the protective cap and thrown away. In this case, the holder can be reused. Inasmuch as the used medical needle is not held and loosened, the danger of hurting the palm of a hand or a finger of the operator with the needle can be avoided.

Although certain preferred embodiments have been shown and described, it should be understood that many changes and modifications may be made therein without departing from the scope of the appended claims.

What is claimed is:

1. A blood collection and/or injection device, comprising:
    a double-ended medical needle including a cannula having opposite pointed ends, and a hub fitted over said cannula;
    a cylindrical holder having a first opening defined in one end thereof and a second opening defined in an opposite end thereof, and end portion of said cannula adapted to be inserted into said first opening with said hub held in said first opening by said cylindrical holder; and
    an evacuated blood collection tube or syringe adapted to be inserted into said holder through said second opening defined in said opposite end of said cylindrical holder, and adapted to be pierced by said end portion of said cannula; and
    said hub having spreading teeth;
    said cylindrical holder comprising:
        a holder casing having chuck teeth spreadable radially outwardly by said spreading teeth of said hub;

a ring having recesses for receiving said spreading teeth, and a cap engaging portion; and cap means for engaging said cap engaging portion of said ring.

2. A blood collection and/or injection device according to claim 1, wherein said hub has a step disposed behind said spreading teeth in the direction of insertion of said hub into said holder casing, said step being engageable by said chuck teeth which are spread radially outwardly by said spreading teeth.

3. A blood collection and/or injection device according to claim 1, wherein:

said ring has a hub support hole defined substantially centrally in one end thereof for supporting said hub;

said recesses open into said hub support hole;

said cap engaging portion of said ring is defined on an outer surface of said ring; and said ring is rotatably, and axially immovably, positionable radially inwardly of flexible walls of said holder casing and said spreading teeth.

4. A blood collection and/or injection device according to claim 1, wherein:

said cap means comprises a noncircular hub insertion hole defined substantially centrally in one end thereof;

said cap means is adapted to be fitted in said first opening in said one end of said cylindrical holder and angularly movable therein; and said cap means further comprises a rib disposed therein and engageable with said cap engaging portion of said ring for angular movement therewith and sliding movement with respect thereto in a direction toward said one end thereof.

5. A blood collection and/or injection device according to claim 1, wherein said double-ended medical needle further comprises a rubber sheath fitted over said end portion of said cannula, and wherein said end portion of said cannula with said rubber sheath fitted thereover is insertable into said first opening of said cylindrical holder.

6. A blood collection and/or injection device, comprising:

a double-ended medical needle including a cannula having opposite pointed ends, and a hub fitted over said cannula;

a cylindrical holder having a first opening defined in one end thereof and a second opening defined in an opposite end thereof, and end portion of said cannula adapted to be inserted in said first opening with said hub held in said first opening by said cylindrical holder; and an evacuated blood collection tube or syringe adapted to be inserted into said cylindrical holder through said second opening defined in said opposite end of said cylindrical holder and adapted to be pierced by said end portion of said cannula; and said hub having an engaging flange;

said cylindrical holder having:

hub support walls disposed around said first opening in said one end of said cylindrical holder, said hub support walls including means for supporting a side wall of said hub;

flexible walls separate from said hub support walls;

chuck teeth projecting rapidly inwardly from distal end portions of said flexible walls; and a fastening ring axially slidably mounted over said hub support walls and said flexible walls; and wherein when said end portion of said cannula is inserted into said first opening in said one end of said cylindrical holder until said engaging flange is held against said hub support walls and thereafter said fastening ring is moved axially, and said chuck teeth are flexed radially inwardly to engage said engaging flange of said hub against dislodgment.

7. A blood collection and/or injection device according to claim 6, wherein said double-ended medical needle further comprises a rubber sheath fitted over said end portion of said cannula, and wherein said end portion of said cannula with said rubber sheath fitted thereover is insertable into said first opening of said cylindrical holder.

8. A holder for a medical needle having a cannula, and a hub fitted over the cannula, said holder comprising:

an end defining a first opening, a portion of said cannula adapted to be inserted into said first opening with said hub held at said end of said holder;

an opposite end defining a second opening adapted to receive therein an evacuated blood collection tube or syringe;

hub support walls disposed around said first opening and including engaging means for supporting a side wall of said hub;

flexible walls disposed around said first opening and separated from said hub support walls by slots, said flexible walls being flexible at least at distal ends thereof; and chuck teeth disposed around said first opening and projecting radially inwardly from said flexible walls near said distal end thereof, said chuck teeth being spreadable radially outwardly by a spreading and engaging means of said hub, and said chuck teeth thereafter engaging said spreading and engaging means of said hub, thereby preventing the medical needle from being removed when said engaging means has moved past said chuck teeth.

9. A holder according to claim 8, wherein said medical needle further comprises a rubber sheath fitted over said end portion of said cannula, and wherein said end portion of said cannula with said rubber sheath fitted thereover is insertable into said first opening of said cylindrical holder.

10. A holder for a medical needle having a cannula, and a hub fitted over the cannula and having spreading teeth, said holder comprising:

an end defining a first opening, a portion of said cannula adapted to be inserted into said first opening with said hub held by an end of said holder;

an opposite end defining a second opening adapted to receive therein an evacuated blood collection tube or syringe;

a holder casing having flexible walls flexible at distal ends thereof, and chuck teeth projecting radially inwardly from distal ends of said flexible walls and spreadable radially outwardly by said spreading teeth of said hub of said medical needle;

a ring having a central hub support hole and disposed rotatably, and axially immovably, inside of said flexible walls and said chuck teeth of said holder casing; and cap means having a central hub inserting hole and fitted angularly movably over said holder casing, said cap means having a rib engageable with said ring for angular movement therewith and sliding movement with respect thereto in a direction toward a distal end thereof.

11. A holder according to claim 10, wherein said medical needle further comprises a rubber sheath fitted over said end portion of said cannula, and wherein said end portion of said cannula with said rubber sheath fitted thereover is insertable into said first opening of said cylindrical holder.

12. A holder for a medical needle having a cannula, and a hub fitted over the cannula, said hub having spreading teeth and a flange, said holder comprising:

an end defining a first opening, a portion of said cannula adapted to be inserted into said first opening with said hub held in said first opening by said holder;

an opposite end defining a second opening adapted to receive therein an evacuated blood collection tube or syringe;

hub support walls disposed around said first opening and including means for supporting a side wall of said hub;

flexible walls disposed around said first opening and separated from said hub support walls by slits, said flexible walls being flexible at least at distal ends thereof;

chuck teeth disposed around said first opening and projecting radially inwardly from said distal ends of said flexible walls; and a fastening ring axially slidably fitted over said hub support walls and said flexible walls; and wherein when said portion of said cannula is inserted into said first opening until said flange of said hub is engaged and held against said hub support walls and thereafter said fastening ring is moved axially, said chuck teeth are flexed radially inwardly to engage said flange of said hub against dislodgement.

13. A holder according to claim 12, wherein said medical needle further comprises a rubber sheath fitted over said end portion of said cannula, and wherein said end portion of said cannula with said rubber sheath fitted thereover is insertable into said first opening of said cylindrical holder.

* * * * *

UNITED STATES PATENT AND TRADEMARK OFFICE
CERTIFICATE OF CORRECTION

PATENT NO. : 5,069,225
DATED : December 3, 1991
INVENTOR(S) : T. OKAMURA

It is certified that error appears in the above-identified patent and that said Letters Patent is hereby corrected as shown below:

Title page, Section [56] References Cited:

Insert under "U.S. PATENT DOCUMENTS" -

--4,740,205   4/1988   Seltzer et al.....604/192--

Insert under "FOREIGN PATENT DOCUMENTS" -

--1 286 690   8/1972   England--

Column 5, line 6, "said" (1st instance) should read --an--.

Column 5, lines 57-58, delete "which is covered with".

Column 6, lines 11-12, delete "which is covered with".

Signed and Sealed this

Twenty-sixth Day of October, 1993

Attest:

BRUCE LEHMAN

Attesting Officer        Commissioner of Patents and Trademarks